Jan. 17, 1939. R. N. RUEDLINGER Plant Pat. 309
PEAR TREE
Filed April 11, 1938
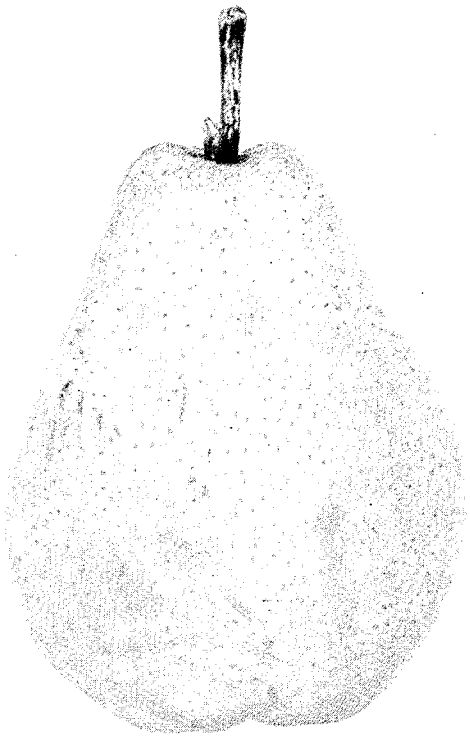
INVENTOR
Rudolf N. Ruedlinger
By Orville M. Kile
PLANT PATENT AGENT Patented Jan. 17, 1939

Plant Pat. 309

UNITED STATES PATENT OFFICE

309

PEAR TREE

Rudolf N. Ruedlinger, St. Louis Park, Minn., assignor to Ruedlinger Nursery, St. Louis Park, Minn.

Application April 11, 1938, Serial No. 201,431

1 Claim. (Cl. 47—62)

My present discovery relates to a new and distinct variety of pear tree and particularly to improved quality of its fruit and its earlier ripening season.

This variety was discovered by me on a farm in northern Wisconsin and is presumably a seedling of which the parents are unknown. After watching the tree and its fruit for three years, I had the tree moved to our nurseries at St. Louis Park. Here I asexually reproduced the variety by grafting and budding and have accumulated a stock of about 1200 trees, none of which has left our possession.

The accompanying illustration shows in full color a specimen of this new variety when ripe.

The Tree

The tree of this variety has no particularly novel features except that it is remarkably sturdy and hardy and is easily grown. The leaves are of medium length and oval in shape. The flowers appear early and in large clusters.

The Fruit

A detailed description of the fruit of my new variety follows:

*Ripening.*—Pears may be picked from this variety about September 1st for the purpose of storing. The ripening season extends to about October 1st. (In Hennepin County, Minnesota.)

*Shape.*—Regular; obovate pyriform; sides equal.

*Size.*—Large; length 3¾ inches, 3 inches across at widest point.

*Basin.*—Shallow, medium wide, flaring, smooth, regular.

*Cavity.*—Medium in depth and width, flaring, smooth, not lipped.

*Calyx.*—Small; closed; calyx lobes medium narrow.

*Calyx tube.*—Funnel form; long; slender.

*Skin.*—Aspect—thin; smooth except where slightly roughened by russet dots; medium glossy. Color—prevailing effect is clear Wax Yellow (Plate XVI, Ridgway's Color Standards and Nomenclature). Is not blushed. Has little or no russet except slight tendency on sunny side where russet may appear in very small irregular spots. Dots—numerous; very small but conspicuous; round or nearly round; russet or greenish.

*Flesh.*—Color—creamy white. Texture—juicy; tender; medium fine grained; quality exceptionally good; slightly granular near the core but not elsewhere. Flavor—mildly sweet; pleasant. Aroma—pleasing; distinct.

*Core.*—Size—small to medium. Character—closed; core lines rather indistinct; generally clasping.

*Seed.*—Small; light brown; medium long; plump.

*Stem.*—Medium heavy; length averages 1¼ inches.

Comparisons

The two known varieties of pear which most resemble my new variety are Beurré D'Anjou and Lawrence, but they differ principally in the following respects:

*Comparison with Beurré D'Anjou*

The fruit of my new variety is slightly less blocky, has longer stems and shows less of a tendency to blush. The core is considerably smaller. The flesh is of much finer quality. The date of ripening is two to three weeks earlier than that of Beurré D'Anjou.

*Comparison with Lawrence*

The fruit of my new variety is considerably larger, less blocky and more tapering toward the stem. The skin is not so thick and has less tendency to russet and blush. The date of ripening is three to four weeks earlier than that of Lawrence.

Having thus disclosed my discovery, I claim:

A new and distinct variety of pear tree characterized particularly by its hardiness and vigor; its early ripening period; and its fruit with distinctive coloring, fine quality of flesh, and small core, substantially as shown and described.

RUDOLF N. RUEDLINGER.